(12) United States Patent
Lechmann et al.

(10) Patent No.: US 7,846,207 B2
(45) Date of Patent: Dec. 7, 2010

(54) INTERVERTEBRAL IMPLANT (75) Inventors: Beat Lechmann, Bettlach (CH);
Dominique Burkard, Gretzenbach (CH); Chris M. J. Cain, Norwood (AU); Claude Mathieu, Zurich (CH)

(73) Assignee: Synthes USA, LLC, West Chester, PA (US)

( * ) Notice: Subject to any disclaimer, the term of this patent is extended or adjusted under 35 U.S.C. 154(b) by 1412 days.

(21) Appl. No.: 11/199,599

(22) Filed: Aug. 8, 2005

(65) Prior Publication Data

US 2006/0085071 A1   Apr. 20, 2006

Related U.S. Application Data

(63) Continuation of application No. PCT/CH03/00089, filed on Feb. 6, 2003.

(51) Int. Cl.
*A61F 2/44* (2006.01)
(52) U.S. Cl. .................. 623/17.11; 623/17.16
(58) Field of Classification Search .............. 606/63, 606/291, 90, 293; 623/17.11, 17.15, 17.16
See application file for complete search history.

(56) References Cited

U.S. PATENT DOCUMENTS 2,621,145 A   12/1952   Sano (Continued)

FOREIGN PATENT DOCUMENTS

CA   2317791 A1   8/1999

DE   30 42 003 A1   7/1982
DE   39 33 459 A1   4/1991

(Continued)

OTHER PUBLICATIONS

Office Notice of Reason of Rejection issued by the Japanese Patent Office.

*Primary Examiner*—Todd E Manahan
*Assistant Examiner*—Lynnsy Schneider
(74) *Attorney, Agent, or Firm*—Stroock & Stroock & Lavan LLP (57) ABSTRACT

An intervertebral implant having a three-dimensional body (10) and a securing plate (1). The three-dimensional body (10) includes an upper side (1) and an underside (2) which are suitable for abutting the end plates of two adjacent vertebral bodies, a left side surface (3) and a right side surface (4), a front surface (5) and a rear surface (6), a horizontal middle plane (7) between the upper side (1) and the underside (2), and a vertical middle plane (12) extending from the front surface (5) to the rear surface (6). The three-dimensional body further includes a plurality of boreholes (9a) passing through the body (10), which are suitable for accommodating longitudinal fixation elements (20). The intervertebral implant also includes a front plate (8) displaceably disposed as an insert with the front side (5) of the three-dimensional body, the front plate (8) having a plurality of boreholes (9) in which the longitudinal fixation elements (20) can be anchored, and whose openings overlap with the openings of the boreholes of the three-dimensional body (10). A securing plate can be fastened essentially parallel to the front plate (8) at the three-dimensional body (10) in such a manner that the boreholes of the front plate (9) are covered at least partly by the securing plate (18). By virtue of the configuration of the intervertebral implant, a rigid, firm connection between the intervertebral implant and the longitudinal fixation elements used to fasten it, is possible.

43 Claims, 6 Drawing Sheets

U.S. PATENT DOCUMENTS

| | | | |
|---|---|---|---|
| 4,135,506 A | 1/1979 | Ulrich | |
| 4,501,269 A | 2/1985 | Bagby | |
| 4,512,038 A | 4/1985 | Alexander et al. | |
| 4,627,853 A | 12/1986 | Campbell et al. | |
| 4,678,470 A | 7/1987 | Nashef et al. | |
| 4,717,115 A | 1/1988 | Schmitz | |
| 4,858,603 A | 8/1989 | Clemow et al. | |
| 4,904,261 A | 2/1990 | Dove et al. | |
| 4,936,851 A | 6/1990 | Fox et al. | |
| 4,950,296 A | 8/1990 | McIntyre | |
| 4,961,740 A | 10/1990 | Ray et al. | |
| 4,978,350 A * | 12/1990 | Wagenknecht | 606/312 |
| 4,994,084 A | 2/1991 | Brennan | |
| 5,026,373 A | 6/1991 | Ray et al. | |
| 5,053,049 A | 10/1991 | Campbell | |
| 5,062,850 A | 11/1991 | MacMillan et al. | |
| 5,084,051 A | 1/1992 | Törmälä et al. | |
| 5,112,354 A | 5/1992 | Sires | |
| 5,192,327 A | 3/1993 | Brantigan | |
| 5,211,664 A | 5/1993 | Tepic et al. | |
| 5,281,226 A | 1/1994 | Davydov et al. | |
| 5,284,655 A | 2/1994 | Bogdansky et al. | |
| 5,298,254 A | 3/1994 | Prewett et al. | |
| 5,314,476 A | 5/1994 | Prewett et al. | |
| 5,348,788 A | 9/1994 | White | |
| 5,405,391 A | 4/1995 | Hednerson et al. | |
| 5,423,817 A | 6/1995 | Lin | |
| 5,439,684 A | 8/1995 | Prewett et al. | |
| 5,458,638 A | 10/1995 | Kuslich et al. | |
| 5,489,308 A | 2/1996 | Kuslich et al. | |
| 5,507,818 A | 4/1996 | McLaughlin | |
| 5,514,180 A | 5/1996 | Heggeness et al. | |
| 5,522,899 A | 6/1996 | Michelson | |
| 5,534,030 A | 7/1996 | Navarro et al. | |
| 5,549,679 A | 8/1996 | Kuslich | |
| 5,554,191 A | 9/1996 | Lahille et al. | |
| 5,556,430 A | 9/1996 | Gendler | |
| 5,569,308 A | 10/1996 | Sottosanti | |
| 5,571,190 A | 11/1996 | Ulrich et al. | |
| 5,571,192 A | 11/1996 | Schönhöffer | |
| 5,607,474 A | 3/1997 | Athanasiou et al. | |
| 5,609,635 A | 3/1997 | Michelson | |
| 5,609,636 A | 3/1997 | Kohrs et al. | |
| 5,609,637 A | 3/1997 | Biedermann et al. | |
| 5,676,699 A | 10/1997 | Gogolewski et al. | |
| 5,683,394 A | 11/1997 | Rinner | |
| 5,683,463 A | 11/1997 | Godefroy et al. | |
| 5,702,449 A | 12/1997 | McKay | |
| 5,702,451 A | 12/1997 | Biedermann et al. | |
| 5,702,453 A | 12/1997 | Rabbe et al. | |
| 5,702,455 A | 12/1997 | Saggar | |
| 5,728,159 A | 3/1998 | Stroever et al. | |
| 5,735,905 A | 4/1998 | Parr | |
| 5,766,253 A | 6/1998 | Brosnahan, III | |
| 5,776,194 A | 7/1998 | Mikol et al. | |
| 5,776,197 A | 7/1998 | Rabbe et al. | |
| 5,776,198 A | 7/1998 | Rabbe et al. | |
| 5,776,199 A | 7/1998 | Michelson | |
| 5,782,915 A | 7/1998 | Stone | |
| 5,785,710 A | 7/1998 | Michelson | |
| 5,800,433 A | 9/1998 | Benzel et al. | 606/61 |
| 5,865,849 A | 2/1999 | Stone | |
| 5,876,452 A | 3/1999 | Athanasiou et al. | |
| 5,885,299 A | 3/1999 | Winslow et al. | |
| 5,888,222 A | 3/1999 | Coates et al. | |
| 5,888,223 A | 3/1999 | Bray, Jr. | 623/17 |
| 5,888,224 A | 3/1999 | Beckers et al. | |
| 5,888,227 A | 3/1999 | Cottle | |
| 5,895,426 A | 4/1999 | Scarborough et al. | |
| 5,899,939 A | 5/1999 | Boyce et al. | |
| 5,902,338 A | 5/1999 | Stone | |
| 5,904,719 A | 5/1999 | Errico et al. | |
| 5,910,315 A | 6/1999 | Stevenson et al. | |
| 5,922,027 A | 7/1999 | Stone | |
| 5,944,755 A | 8/1999 | Stone | |
| 5,968,098 A | 10/1999 | Winslow | |
| 5,972,368 A | 10/1999 | McKay | |
| 5,976,187 A | 11/1999 | Richelsoph | |
| 5,980,522 A | 11/1999 | Koros et al. | |
| 5,981,828 A | 11/1999 | Nelson et al. | |
| 5,984,967 A | 11/1999 | Zdeblick et al. | |
| 5,989,289 A | 11/1999 | Coates et al. | |
| 6,013,853 A | 1/2000 | Athanasiou et al. | |
| 6,025,538 A | 2/2000 | Yaccarino, III | |
| 6,033,405 A | 3/2000 | Winslow et al. | |
| 6,033,438 A | 3/2000 | Bianchi et al. | |
| 6,039,762 A | 3/2000 | McKay | |
| 6,045,579 A | 4/2000 | Hochshuler et al. | |
| 6,045,580 A | 4/2000 | Scarborough et al. | |
| 6,080,158 A | 6/2000 | Lin | |
| 6,080,193 A | 6/2000 | Hochshuler et al. | |
| 6,090,998 A | 7/2000 | Grooms et al. | |
| 6,096,081 A | 8/2000 | Grivas et al. | |
| 6,110,482 A | 8/2000 | Khouri et al. | |
| 6,123,731 A | 9/2000 | Boyce et al. | |
| 6,129,763 A | 10/2000 | Chauvin et al. | |
| 6,143,030 A | 11/2000 | Schroder | |
| 6,143,033 A | 11/2000 | Paul et al. | |
| 6,156,070 A | 12/2000 | Incavo et al. | |
| 6,193,756 B1 | 2/2001 | Studer et al. | |
| 6,200,347 B1 | 3/2001 | Anderson et al. | |
| 6,206,922 B1 | 3/2001 | Zdeblick et al. | |
| 6,231,610 B1 | 5/2001 | Geisler | |
| 6,235,059 B1 | 5/2001 | Benezech et al. | |
| 6,241,769 B1 | 6/2001 | Nicholson et al. | |
| 6,245,108 B1 | 6/2001 | Biscup | |
| 6,258,125 B1 | 7/2001 | Paul et al. | |
| 6,261,586 B1 | 7/2001 | McKay | |
| 6,264,695 B1 | 7/2001 | Stoy | |
| 6,270,528 B1 | 8/2001 | McKay | |
| 6,322,562 B1 * | 11/2001 | Wolter | 606/62 |
| 6,342,074 B1 | 1/2002 | Simpson | |
| 6,364,880 B1 | 4/2002 | Michelson | |
| 6,423,063 B1 | 7/2002 | Bonutti | |
| 6,432,106 B1 | 8/2002 | Fraser | |
| 6,458,158 B1 | 10/2002 | Anderson et al. | |
| 6,468,311 B2 | 10/2002 | Boyd et al. | |
| 6,569,201 B2 | 5/2003 | Moumene et al. | |
| 6,638,310 B2 | 10/2003 | Lin et al. | |
| 6,645,212 B2 * | 11/2003 | Goldhahn et al. | 606/291 |
| 6,761,739 B2 | 7/2004 | Shepard | |
| 6,884,242 B2 * | 4/2005 | LeHuec et al. | 606/86 B |
| 6,972,019 B2 * | 12/2005 | Michelson | 606/86 A |
| 6,984,234 B2 | 1/2006 | Bray | 606/69 |
| 7,112,222 B2 | 9/2006 | Fraser et al. | |
| 7,172,627 B2 * | 2/2007 | Fiere et al. | 623/17.11 |
| 7,232,464 B2 | 6/2007 | Mathieu et al. | 623/17.11 |
| 2001/0001129 A1 | 5/2001 | McKay et al. | |
| 2001/0005796 A1 | 6/2001 | Zdeblick et al. | |
| 2001/0010021 A1 | 7/2001 | Boyd et al. | |
| 2001/0016777 A1 | 8/2001 | Biscup | |
| 2001/0031254 A1 | 10/2001 | Bianchi et al. | |
| 2001/0039456 A1 | 11/2001 | Boyer, II et al. | |
| 2001/0041941 A1 | 11/2001 | Boyer, II et al. | |
| 2002/0010511 A1 | 1/2002 | Michelson | |
| 2002/0022843 A1 | 2/2002 | Michelson | 606/70 |
| 2002/0029084 A1 | 3/2002 | Paul et al. | |
| 2002/0082597 A1 | 6/2002 | Fraser | |
| 2002/0082603 A1 * | 6/2002 | Dixon et al. | 606/69 |
| 2002/0091447 A1 | 7/2002 | Shimp et al. | |
| 2002/0099376 A1 | 7/2002 | Michelson | 606/61 |
| 2002/0106393 A1 | 8/2002 | Bianchi et al. | |
| 2002/0111680 A1 | 8/2002 | Michelson | |
| 2002/0147450 A1 | 10/2002 | LeHuec et al. | 606/61 |

| | | | |
|---|---|---|---|
| 2002/0169508 A1 | 11/2002 | Songer et al. | 623/17.11 |
| 2002/0193880 A1* | 12/2002 | Fraser | 623/17.11 |
| 2003/0078668 A1* | 4/2003 | Michelson | 623/17.16 |
| 2003/0125739 A1 | 7/2003 | Bagga et al. | |
| 2004/0210314 A1 | 10/2004 | Michelson | |
| 2005/0033433 A1 | 2/2005 | Michelson | |
| 2007/0219635 A1 | 9/2007 | Mathieu et al. | 623/17.16 |

FOREIGN PATENT DOCUMENTS

| | | |
|---|---|---|
| DE | 42 42 889 A1 | 6/1994 |
| DE | 44 09 392 A1 | 9/1995 |
| DE | 195 04 867 C1 | 2/1996 |
| DE | 299 13 200 U1 | 9/1999 |
| EP | 0505634 A1 | 9/1992 |
| EP | 0517030 A2 | 12/1992 |
| EP | 0577178 A1 | 1/1994 |
| EP | 0639351 A2 | 2/1995 |
| EP | 0505634 B1 | 8/1997 |
| EP | 0966930 | 12/1999 |
| EP | 0968692 A1 | 1/2000 |
| EP | 0906065 B1 | 1/2004 |
| FR | 2 697 996 | 5/1994 |
| FR | 2 700 947 | 8/1994 |
| FR | 2 753 368 | 3/1998 |
| GB | 2 148 122 A | 5/1985 |
| SU | 1465040 A1 | 3/1989 |
| WO | WO 88/03417 | 5/1988 |
| WO | WO 88/10100 | 12/1988 |
| WO | WO 92/01428 | 2/1992 |
| WO | WO 95/21053 | 8/1995 |
| WO | WO 96/39988 | 12/1996 |
| WO | WO 97/20526 | 6/1997 |
| WO | WO 97/25941 | 7/1997 |
| WO | WO 97/25945 | 7/1997 |
| WO | WO 97/39693 | 10/1997 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/29271 | 6/1999 |
| WO | WO 99/32055 | 7/1999 |
| WO | WO 99/38461 | 8/1999 |
| WO | WO 99/38463 | 8/1999 |
| WO | WO 99/56675 | 11/1999 |
| WO | WO 99/63914 | 12/1999 |
| WO | WO 00/07527 | 2/2000 |
| WO | WO 00/07528 | 2/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/66044 A1 | 11/2000 |
| WO | WO 00/66045 A1 | 11/2000 |
| WO | WO 00/74607 A1 | 12/2000 |
| WO | WO 01/08611 | 2/2001 |
| WO | WO 01/56497 A2 | 8/2001 |
| WO | WO 01/93742 A2 | 12/2001 |
| WO | WO 01/95837 A1 | 12/2001 |

* cited by examiner

INTERVERTEBRAL IMPLANT

CROSS REFERENCE TO RELATED APPLICATION

This application is a continuation of International Patent Application No. PCT/CH2003/000089, filed Feb. 6, 2003, the entire contents of which is expressly incorporated herein by reference.

TECHNICAL FIELD

The present invention relates generally to intervertebral implants.

BACKGROUND OF THE INVENTION

GB-A-2 207 607 discloses an intervertebral implant, which has a horseshoe-shaped configuration with a plurality of cylindrical holes. The holes are smooth on the inside and only have a stop for the heads of the bone screws, which are to be introduced therein. A disadvantage of this arrangement is that the fastening screws, introduced therein, can be anchored only with their shaft in the bone. This does not result in a rigid connection with the horseshoe-shaped intervertebral implant. When the anchoring of the screw shaft in the bone is weakened, the intervertebral implant becomes movable with respect to the screw and the bone screws tend to migrate, endangering the blood vessels. Moreover, the loosening of the intervertebral implant can lead to a pseudoarthrosis.

U.S. Patent Publication US-A 2000/0010511 (Michelson) discloses an intervertebral implant, which, at its front surface, has two boreholes with an internal thread, into which bone screws with a threaded head can be introduced. A disadvantage of this implant is that the bone screws can become loose and are not secured against being screwed out or falling out. A further disadvantage is that the bone screws are fastened completely to the implant body itself and that therefore the latter experiences a relatively large stress.

Screws which emerge at the anterior or anterolateral edge of the vertebral body because of loosening run the risk of injuring main vessels such as the aorta and Vena cava, as well as supply vessels such as lumbar arteries and veins. Injury to these main vessels may result in internal bleeding possibly causing death within a very short time. Loosening of screws is more likely when they are not mounted angularly firmly.

SUMMARY OF THE INVENTION

The present invention is to provide a remedy for the above-discussed disadvantages. The present invention is directed to an intervertebral implant which can enter into a permanent, rigid connection with bone fixation means, so that, even if the bone structure is weakened, there is no loosening between the intervertebral implant and the bone fixation means. Moreover, over a separately constructed front plate, there is tension chording for the bone fixation elements, so that the implant body experiences less stress, that is, superimposed tensions. Moreover, a securing plate enables all bone fixation elements to be secured simultaneously.

The present invention accomplishes the objective set out above with an intervertebral implant, comprising a three-dimensional body having an upper side and an under side which are suitable for abutting the end plates of two adjacent vertebral bodies. The three-dimensional body further includes a left side surface and a right side surface, a front surface and a rear surface, a horizontal middle plane between the upper side and the under side, and a vertical middle plane extending from the front surface to the rear surface. The three-dimensional body further comprising a plurality of boreholes, having openings at least at or near the front surface, passing there through and being suitable for accommodating longitudinal fixation elements. The intervertebral implant further including a front plate displaceably disposed as an insert with the front side of the three-dimensional body, where the front plate includes a plurality of boreholes having openings and in which the longitudinal fixation elements can be anchored, and whose openings overlap with the openings of the boreholes of the three-dimensional body. The intervertebral implant has a securing plate fastened substantially parallel to the front plate in such a manner that the boreholes of the front plate are covered at least partly by the securing plate. An advantage achieved by the present invention, arises essentially from the solid connection between the intervertebral implant and the longitudinal fixation elements, used to fasten it.

Compared to the two-part implants of the state of the art, for which a front plate is implanted in a separate step, the present invention has the advantage that the implantation of the intervertebral implant may be carried out in one step and, with that, can be carried out more easily and more quickly. A further advantage is that the intervertebral implant is fixed as frontally as possible at the body of the vertebra. That is, at a place where good bone material usually is present. The result is an anterior movement limitation without a greater risk to the surrounding structures. The load is still absorbed under compression by the intervertebral implant and not by the front plate or the fixation screws (longitudinal fixation elements).

A method for implanting an intervertebral implant of the present invention between two adjacent vertebral bodies includes introducing the intervertebral implant, having a three-dimensional body, a front plate, and one or more boreholes, between two adjacent vertebral bodies, attaching longitudinal fixation elements with heads through the boreholes into the vertebral bodies, and attaching a securing plate by means of a fastening agent over the heads of the longitudinal fixation elements to the front plate, such that the heads of the longitudinal fixation elements are captured between the front plate and the securing plate wherein the longitudinal fixation elements are secured against being shifted relative to the intervertebral implant.

Other objectives and advantages in addition to those discussed above will become apparent to those skilled in the art during the course of the description of a preferred embodiment of the invention which follows. In the description, reference is made to accompanying drawings, which form a part thereof, and which illustrate an example of the invention. Such example, however, is not exhaustive of the various embodiments of the invention, and therefore, reference is made to the claims that follow the description for determining the scope of the invention.

DESCRIPTION OF THE PREFERRED EMBODIMENTS

The intervertebral implant, shown in FIG. 1-7, includes a three-dimensional body 10 in the form of a cage with an upper side 1 and an underside 2, which are suitable for abutting the end plates of two adjacent vertebral bodies, a left side surface 3 and a right side surface 4, a front surface 5 and a back surface 6, a horizontal middle plane 7 located between the upper side 1 and the underside 2, a vertical middle plane 12 extending from the front surface 5 to the rear surface 6 and four boreholes 9a, which pass through the body 10 and are suitable for accommodating longitudinal fixation elements 20. The body 10 may be constructed as a hollow body, the mantle surfaces of which are provided with perforations 19. The upper side 1 and/or under side 2 of the intervertebral implant may preferably be convex in shape, not planar. A convex shape to the upper side 1 and the underside 2 allows for an improved fit with the end plates of the adjacent vertebral bodies by the intervertebral implant. Further, the side surfaces 1-6 of the intervertebral implant may be essentially convex, as well.

Figure 7:
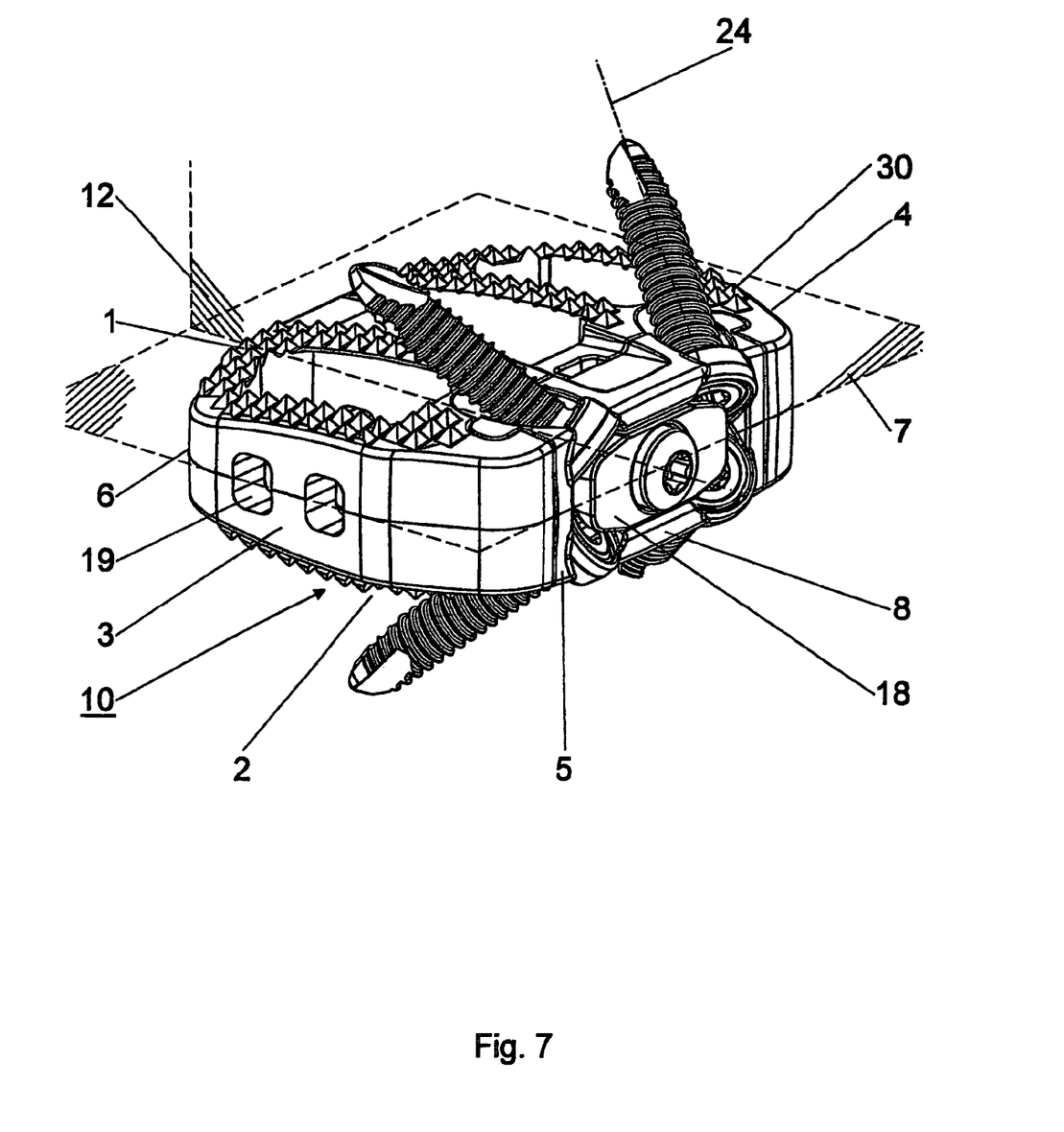
FIG. 7 shows a completely installed intervertebral implant with front plate and securing plate.

As shown in FIG. 7, the upper side 1 and the underside 2 of the three-dimensional body 10 are provided with structuring in the form of teeth 30.

Figure 5:
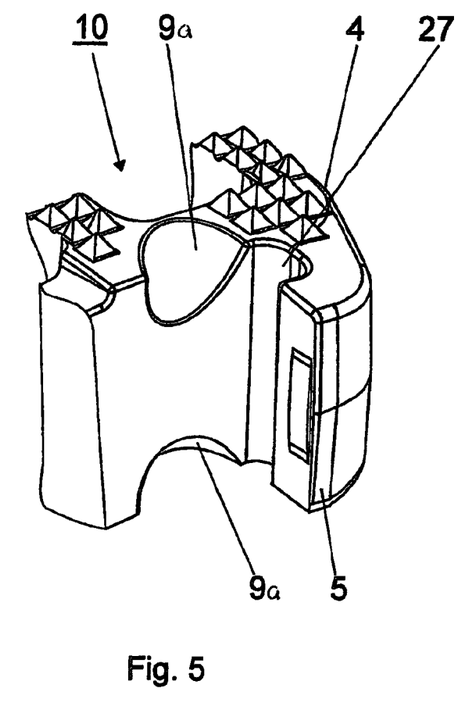
FIG. 5 shows a three-dimensional detailed representation of the body of the intervertebral implant, which shows the connecting elements to the front plate of FIG. 6.
Figure 6:
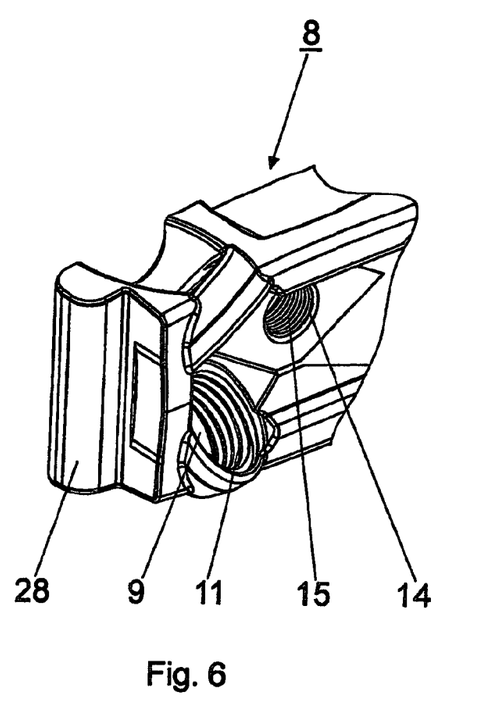
FIG. 6 shows a three-dimensional detailed representation of the front plate of the intervertebral implant and the connecting elements to the body of FIG. 5

At the front surface of the three-dimensional body 10, a front plate 8 may be mounted, which is disposed perpendicular to the horizontal central plane of the intervertebral implant and through which four boreholes 9 pass and in which the longitudinal fixation elements 20 can be anchored. The front plate 8, as shown in FIGS. 5 and 6, is constructed as an insert for the three-dimensional body 10. The three-dimensional body 10 has a semicircular groove 27 extending parallel to the vertical middle plane 12 at the transitions of the left side surface 3 and the right side surface 4 (FIG. 5) to the front surface 5. Correspondingly, the front plate 8 has right and left (FIG. 6) similarly extending and similarly dimensioned, semicircular rail 28. As a result, the front plate can be pushed and positioned easily with its two lateral rails 28 into the corresponding grooves 27 of the body 10 during the production of the intervertebral implant.

In one embodiment, at least one of the boreholes 9 in the front plate is constructed so that a longitudinal fixation element 20, accommodated therein, can be connected rigidly with the front plate. A rigid connection may be accomplished, for example, owing to the fact that at least one of the boreholes 9 of the front plate 8 has an internal thread. A corresponding longitudinal fixation element 20, bone screw, with a threaded end can then be screwed together rigidly with the implant. In an alternative embodiment, the four boreholes 9 in the front plate may have an internal thread 11, so that longitudinal fixation elements 20 can be connected rigidly with the front plate 8.

As discussed, the front plate 8 may be disposed, preferably vertically to the horizontal central plane, so that it can be displaced vertically with respect to the three-dimensional body 10. By these means, "stress shielding" (protection and neutralization of mechanical stresses) is attained, which permits the end plates to be adapted to the intervertebral implant during the healing process.

The intervertebral implant may have a securing plate 18, which can be fastened by means of a screw connection parallel to the front plate 8 at the front plate 8 in such a manner that the boreholes 9 of the front plate 8 are partly covered by the securing plate 18. The securing plate 18 may have a central borehole 17 provided, preferably, with an internal thread. Corresponding thereto, the front plate 8 has a central borehole 15 for accommodating fastening means 16. Preferably, the central borehole 15 has an internal thread 14 for accommodating a fastening means 16 in the form of a screw. The securing plate 18 may also be fastened by a bayonet catch or a click catch. By fastening the securing plate 18 to the front plate 8, the heads 21 of the longitudinal fixation elements 20 (discussed later) are contacted by the securing plate 18, so that they are secured against being ejected or screwed out.

Figure 3:
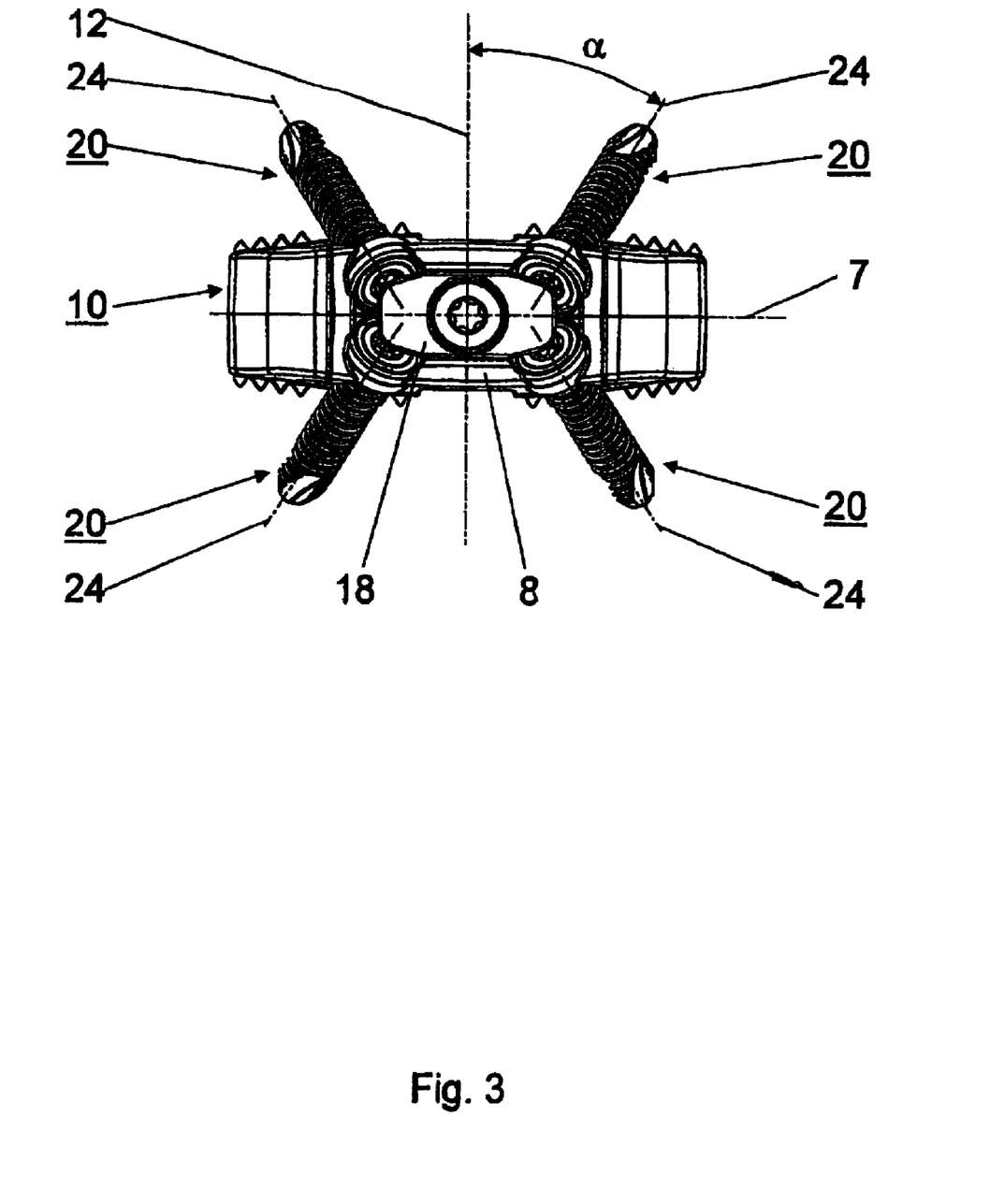
FIG. 3 shows an elevation of the intervertebral implant of FIG. 1.
Figure 4:
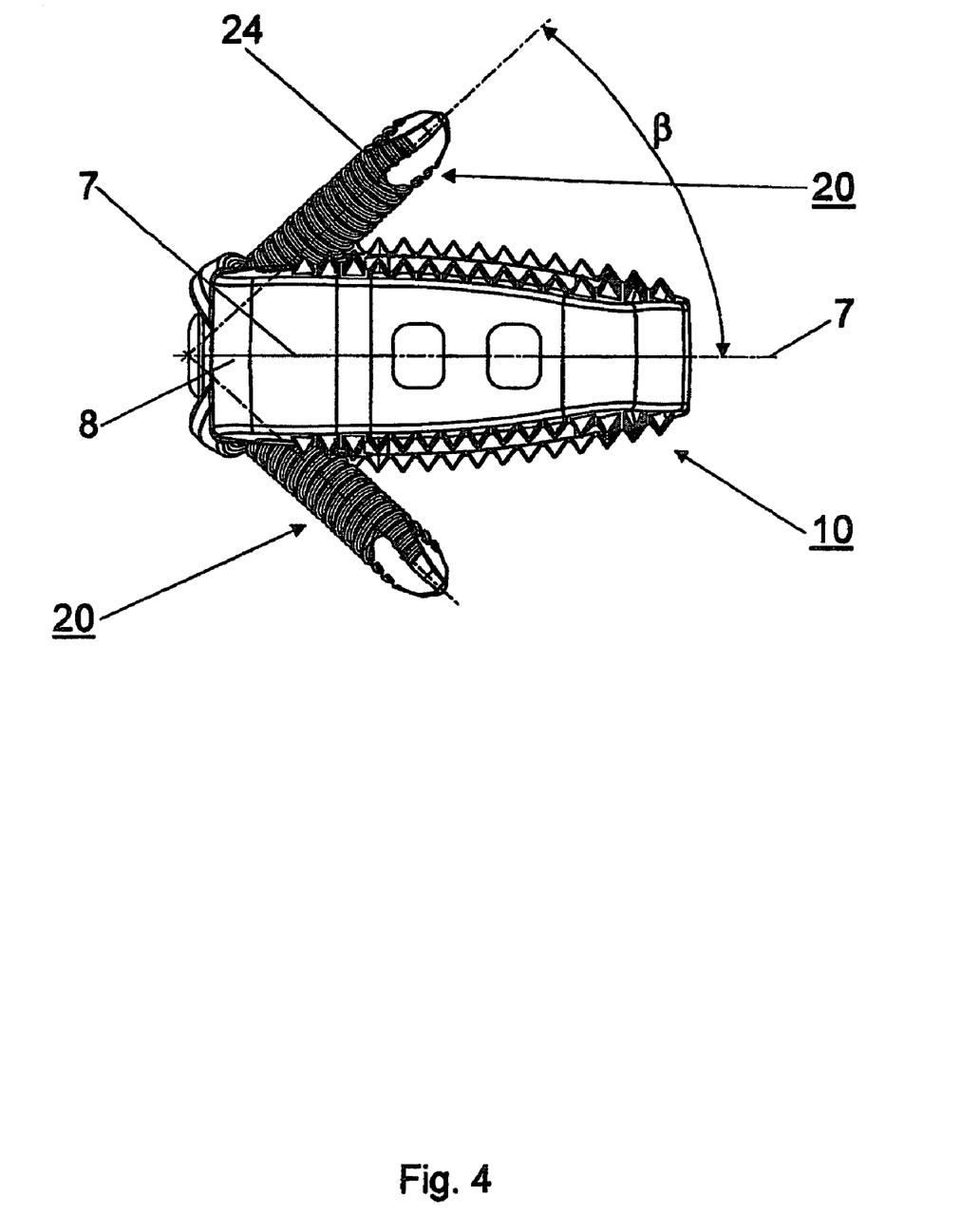
FIG. 4 shows a side view of the intervertebral implant of FIG. 1.

Preferably, the boreholes 9a of the three-dimensional body 10 do not pass either through the left side surface 3 or the right side surface 4 or completely through the front surface 5. The front surface 5, preferably, is also not crossed by the boreholes 9a. Further, the horizontal middle plane 7 is not pierced by the boreholes 9a. Only the axes 24 of the longitudinal fixation elements 20, introduced therein, intersect the horizontal middle plane 7 of the body 10. As seen from the front surface 5, the boreholes of the three-dimensional body 10 and the front plate diverge. The axes 24 of the boreholes of the three-dimensional plate 10 and the front plate 8 enclose an angle β ranging from 20° to 60°, specifically from 36° to 48°, and more preferably an angle β of 42° with the horizontal middle plane 7 (FIG. 4) and an angle α ranging from 10° to 45°, specifically from 27° to 33°, and more preferably an angle α of 30° with the vertical middle plane 12 (FIG. 3). Thus, better access for introducing the screws is achieved.

In one embodiment, at least one of the boreholes 9 of the front plate 8 may taper conically towards the underside 2, so that a bone screw, with a corresponding conical head, can be anchored rigidly therein. The conical borehole preferably has a conical angle, which is smaller than the resulting frictional angle. Advisably, the conicity of the conical borehole is 1:3.75 to 1:20.00 and preferably 1:5 to 1:15.

In another configuration, at least two of the boreholes 9 of the front plate 8 extend parallel to each other. This makes insertion of the intervertebral implant easier. In another embodiment, at least two of the boreholes 9 of the front plate 8 diverge when viewed from the front side. By these means, a region of the vertebral body, which has a better bone quality than does the center of the vertebral body, is reached by the bone screws.

To improve the anchoring of the bone screw in a plastic body of the intervertebral implant (discussed later), a metal sleeve with an internal thread (not shown) may be inserted in the boreholes of the front plate and three-dimensional body. The intervertebral implant may also consist only partially of an x-ray transparent plastic and, in the region of the boreholes consist of a metal, such as titanium or a titanium alloy. Improved guidance and anchoring of the bone screws in the intervertebral implant may be achieved. Further, the boreholes 9 may have a smooth internal wall, into which the threaded head of a metallic, longitudinal fixation element may cut or be molded.

Depending on circumstances, two, three, four or more longitudinal fixation elements may be connected rigidly with the intervertebral implant. Preferably, at least one fixation element should pierce the upper side and at least one fixation element the underside of the intervertebral implant. The longitudinal fixation elements 20 may have either a smooth head, so that there will not be a rigid connection with the implant or a threaded, conical or expendable end, so that there will be a rigid connection with the implant. In both cases, however, the longitudinal fixation elements 20 are secured by the securing plate against rotating out, being ejected out or falling out at a later time.

Figure 1:
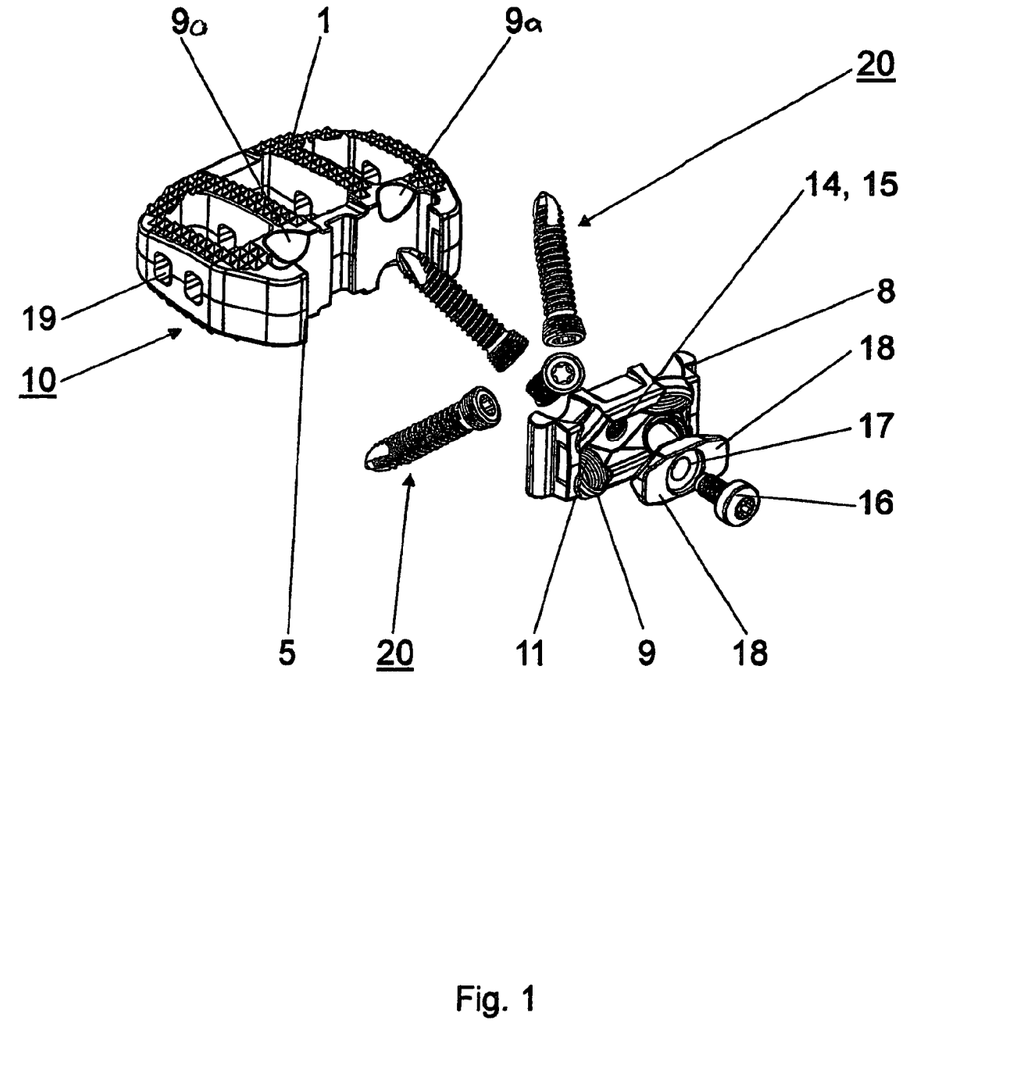
FIG. 1 shows an exploded drawing of the intervertebral implant.
Figure 2:
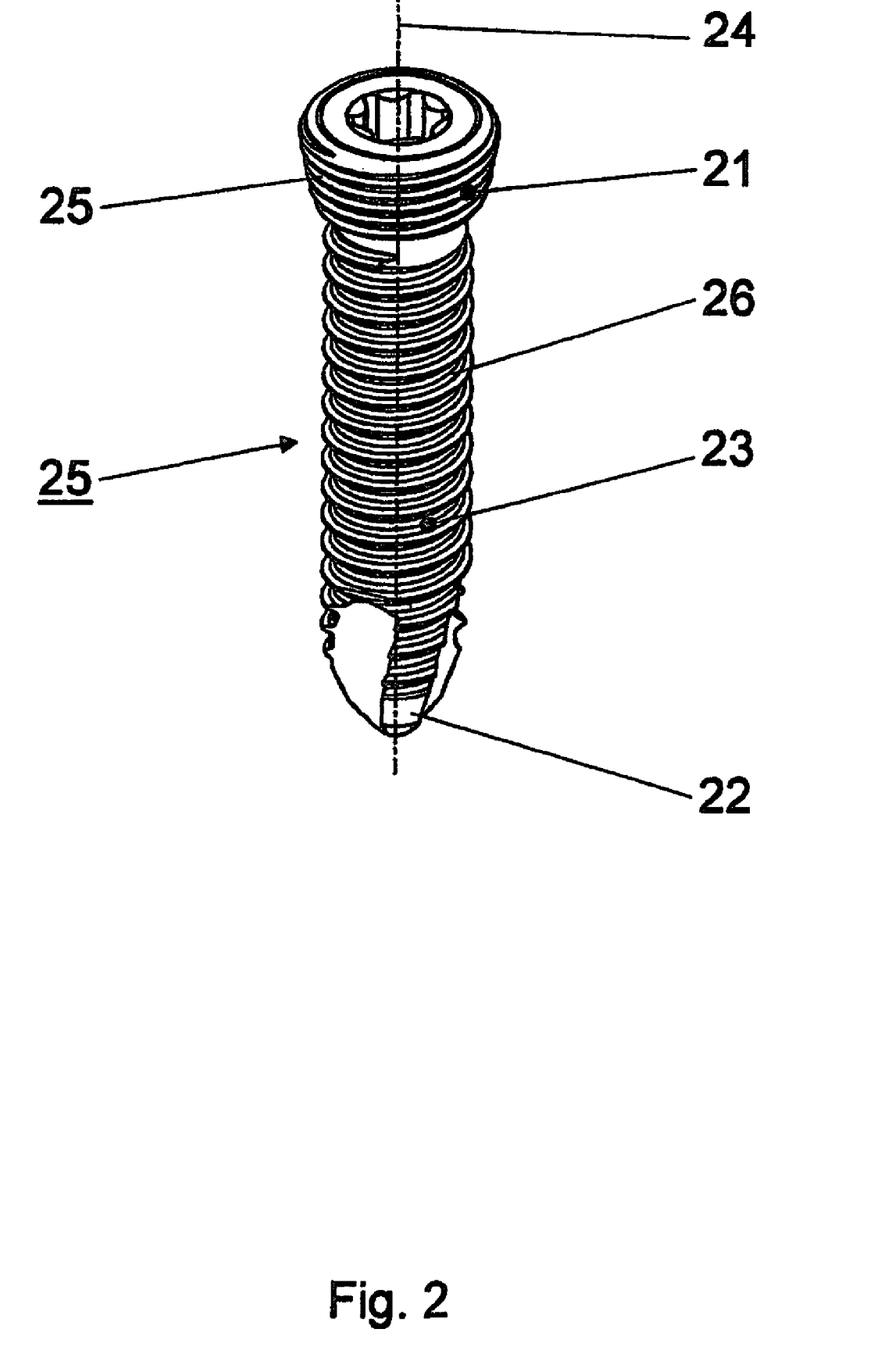
FIG. 2 shows a longitudinal fixation element in the form of a screw.

The longitudinal fixation elements 20 are preferably constructed as bone screws. As shown in FIG. 2, the longitudinal fixation elements 20, introduced into the boreholes 9, have a head 21, a tip 22, a shaft 23 and an axis 24. The head 21 may preferably be provided with an external thread 25, which corresponds to the internal thread 11 of the borehole 9, so that the heads 21 can be anchored in the boreholes 9 in a rigid manner. The shaft 23 may be provided with a thread 26, which is self-drilling and self-cutting. The load thread angle of the thread 26 has a range of between 11° to 14°, preferably between 12° and 13°, and more preferably a load thread angle of 12.5°. The pitch angle of the thread may have a range of between 6° and 10°, preferably between 7° and 9°, and more preferably have a pitch angle of 8°. The special pitch angle produces a self-retardation in the thread, thus ensuring that the bone screw will not automatically become loose.

In the case of a second, possibly rigid type of connection, a longitudinal fixation element 20, bone screw, may preferably be used, the head of which tapers conically towards the shaft, the conicity of the head corresponding to the conicity of the borehole of the intervertebral implant. The longitudinal fixation elements may also be constructed as threadless cylindrical pins, which are provided with a drilling tip, preferably in the form of a trocar. A further variation consist therein that the longitudinal fixation elements are constructed as spiral springs. Finally, the longitudinal fixation elements may also be constructed as single-vaned or multi-vaned spiral blades.

As shown in FIG. 7, two longitudinal fixation elements 20 pierce the upper side 1 and two longitudinal fixation elements 20 pierce the underside 2 of the body 10, thereby anchoring the intervertebral implant to the adjacent vertebral bodies.

The intervertebral implant may be produced from any material which is compatible with the body. Preferably, the three-dimensional body 10 may consist of a body-compatible plastic which has not been reinforced and which may be transparent to x-rays. The advantage over fiber-reinforced plastics, which are already known in implant technology, is that no reinforcing fibers are exposed. Such exposure may be disadvantageous clinically. In such a three-dimensional body 10 constructed of a plastic that has not been reinforced, the use bone screws may be preferable. As discussed previously, the external thread of the bone screw(s) may have a load thread angle range of 11° to 14°, and preferably between 12° to 13°. A comparatively slight inclination of the load flank brings about a high clamping force. As a result, radial expansion and the danger of forming cracks in the plastic are reduced. Furthermore, the external thread of the bone screw(s) may preferably have a pitch angle between 6° and 10° and preferably between 7° and 9'.

The front plate 8 may be made from materials different than the three-dimensional body 10. The front plate 8 is preferably made from a metallic material. Titanium or titanium alloys are particularly suitable as metallic materials. The complete tension chord arrangement (front plate and screws) may also be made from implant steel or highly alloyed metallic materials, such as CoCrMo or CoCrMoC. The advantage of titanium lies in that there is good tissue compatibility and the good ingrowing behavior of bones. The advantage of highly alloyed metallic materials lies in their high-strength values, which permit filigree constructions.

A brief description of a surgical procedure follows in order to explain the invention further.

The intervertebral implant, in the form of a three-dimensional body 10, is introduced between two adjacent vertebral bodies by means of a suitable instrument. Longitudinal fixation elements 20, in the form of bone screws, securing the three-dimensional body 10 are screwed/inserted by means of a suitable aiming device through the boreholes 9 of the front plate 8 into the vertebral bodies. The front plate 8 may be displaced vertically with respect to the three-dimensional body 10, such that the openings of the boreholes 9a of the three-dimensional plate 10 and the boreholes 9 of the front plate 8 overlap, to obtain stress shielding. The securing plate 18 is fastened by means of the fastening agent 16 in the form of a screw over the heads 21 of the longitudinal fixation elements 20 at the front plate 8, so that the heads 21 of the longitudinal fixation elements 20 and, with that, the screws themselves, are captured between the front plate 8 and the securing plate 18 and secured against being shifted relative to the three-dimensional body 10 (for example, by falling out or by turning out). The fastening agent 16, in the form of a screw, preferably is provided with a thread, which is distinguished by a large self-retardation.

The invention claimed is:

1. An intervertebral implant for insertion into an intervertebral disc space between endplates of adjacent vertebral bodies, the implant comprising:
   a three-dimensional body having an upper side and an underside provided with teeth, the upper side and underside suitable for abutting the end plates of the adjacent vertebral bodies, the upper side defining an upper plane and the underside defining an underside plane, a left side surface and a right side surface, a front surface including first and second partial boreholes, a rear surface, a horizontal middle plane between the upper side and the underside, and a vertical middle plane extending from the front surface to the rear surface;
   a front plate mounted to the front surface of the three-dimensional body, the front plate including a first borehole and a second borehole having openings, the first borehole and the second borehole each being aligned with a respective first and second partial borehole;
   first and second fixation elements being anchorable within the first and second boreholes and the first and second partial boreholes, respectively, the first and second fixation elements having first and second heads and first and second shafts, respectively, the first and second heads and the first and second boreholes and partial boreholes positioned substantially between the upper and underside planes in an assembled configuration, the first and second shafts being positioned substantially on an opposite side of the upper and underside planes, respectively, in the assembled configuration; and
   a securing plate fastened substantially parallel to the front plate in such a manner that the first and second boreholes of the front plate and the first and second heads are covered at least partly by the securing plate.

2. The intervertebral implant according to claim 1, wherein the securing plate is fastened parallel to the front plate, by at least one of a screw connection, a bayonet catch or a click catch.

3. The intervertebral implant according to claim 1, wherein the securing plate has a central borehole.

4. The intervertebral implant according to claim 3, wherein the front plate has a central borehole for accommodating a fastening agent.

5. The intervertebral implant according to claim 1, wherein at least one of the first and second boreholes includes internal threads.

6. The intervertebral implant according to claim 5, wherein the first and second boreholes are tapered conically in the direction of the underside of the three-dimensional body.

7. The intervertebral implant according to claim 6, wherein the first and second boreholes have a conical angle, which is smaller than a resulting angle of friction.

8. The intervertebral implant according to claim 7, wherein a conicity of the first and second boreholes range from 1:3.75 to 1:20.00.

9. The intervertebral implant according to claim 7, wherein a conicity of the first and second boreholes range from 1:5 to 1:15.

10. The intervertebral implant according to claim 1, wherein the front plate is preferably disposed vertically relative to the horizontal middle plane.

11. The intervertebral implant according to claim 10, wherein the front plate is disposed in the three-dimensional body, such that it can be shifted vertically relative to the middle plane.

12. The intervertebral implant according to claim 1, wherein the front plate is constructed of a material, which is different from that of the three-dimensional body and is metallic.

13. The intervertebral implant according to claim 1, wherein the side surfaces are constructed convexly.

14. The intervertebral implant according to claim 1, wherein at least one of the upper side and underside are not planar and are constructed convexly.

15. The intervertebral implant according to claim 1, wherein the partial boreholes of the three-dimensional body do not pass completely through the front surface.

16. The intervertebral implant according to claim 1, wherein the first and second boreholes of the front plate diverge when viewed from the front surface.

17. The intervertebral implant according to claim 1, wherein axes of the first and second boreholes define an angle β, ranging from 20° to 60° with the horizontal middle plane.

18. The intervertebral plant according to claim 1, wherein axes of the first and second boreholes enclose an angle α ranging from 10° to 45° with the vertical middle plane.

19. The intervertebral implant according to claim 1, wherein the three-dimensional body consists of a reinforced plastic.

20. The intervertebral implant according to claim 1, wherein the three-dimensional body consists partly of a material which is transparent to x-rays.

21. The intervertebral implant according to claim 1, wherein the first and second boreholes of the front plate have a smooth inner wall, and the first and second heads of the first and second fixation elements include external threads for embedding in the smooth inner walls of the first and second boreholes.

22. The intervertebral implant according to claim 1, wherein the three-dimensional body is constructed as a hollow body and includes casing surfaces which are provided with perforations.

23. The intervertebral implant according to claim 1, wherein the first and second heads are in contact with the securing plate in the assembled configuration.

24. The intervertebral implant according to claim 23, wherein each of the first and second fixation elements include an axis, the axes of the first and second fixation elements intersect the horizontal middle plane of the three-dimensional body.

25. The intervertebral implant according to claim 1, wherein the first fixation element pierces the upper side and the second fixation element pierces the underside.

26. The intervertebral implant according to claim 1, wherein the first and second boreholes include internal threads and the first and second heads of the first and second fixation elements are provided with an external thread, which is threadably matable with the internal threads of the first and second boreholes.

27. The intervertebral implant according to claim 1, wherein the first and second heads taper conically toward the first and second shafts, respectively.

28. The intervertebral implant according to claim 1, wherein the first fixation element passes through the upper side and the second fixation element passes through the underside.

29. The intervertebral implant according to claim 1, wherein the first and second fixation elements are constructed as bone screws, the first and second shafts including a thread capable of self-drilling and self-cutting.

30. The intervertebral implant according to claim 1, wherein the first and second fixation elements are constructed as a threadless cylindrical pins with a drill tip.

31. The intervertebral implant according to claim 1, wherein the first and second fixation elements are constructed as spiral springs.

32. The intervertebral implant according to claim 1, wherein the first and second fixation elements are constructed as single-vaned or multi-vaned spiral blades.

33. The intervertebral implant according to claim 1, wherein the first and second shafts of the first and second fixation elements include a plurality of threads having a load thread angle of 11° to 14°.

34. The intervertebral implant according to claim 1, wherein the first and second shafts of the first and second fixation elements include a plurality of threads having a pitch angle ranging from 6° to 10°.

35. The intervertebral implant according to claim 1, wherein axes of the first and second boreholes define an angle β, ranging from 36° to 48, with the horizontal middle plane.

36. The intervertebral plant according to claim 1, wherein axes of the first and second boreholes enclose an angle α ranging from 27° to 33° with the vertical middle plane.

37. The intervertebral implant according to claim 1, wherein the front surface of the three-dimensional body includes a recess for receiving the front plate.

38. A method for implanting an intervertebral implant between first and second adjacent vertebral bodies, said method comprising the steps of:
 (a) introducing the intervertebral implant between the first and second adjacent vertebral bodies, the implant comprising:
  a three-dimensional body having first and second partial boreholes extending through a front surface, an upper side and an underside including teeth, the upper side defining an upper plane and the underside defining an underside plane, and
  a front plate having first and second boreholes which are aligned with the first and second partial boreholes, respectively, the first and second boreholes and first and second partial boreholes being positioned substantially between the upper and underside planes;
 (b) attaching a first fixation element having a first head portion and a first shaft portion through the first borehole of the front plate, through the first partial borehole of the three-dimensional body, and into the first vertebral body;

(c) attaching a second fixation element having a second head portion and a second shaft portion through the second borehole of the front plate, through the second partial borehole of the three-dimensional body, and into the second vertebral body; and (d) attaching a securing plate with a fastening agent over the first and second head portions of the first and second fixation elements to the front plate, such that the first and second head portions of the first and second fixation elements are captured between the front plate and the securing plate wherein the first and second fixation elements are secured against being shifted relative to the intervertebral implant.

39. The method according to claim 38, wherein the front surface of the three-dimensional body includes a recess for receiving the front plate.

40. An intervertebral implant for mounting between adjacent vertebral bodies including a first vertebral body and a second vertebral body, the intervertebral implant comprising:

a body defining a horizontal middle plane, the body having an upper side including teeth for abutting the first vertebral body and an underside having teeth for abutting the second vertebral body, the upper side defining an upper plane and the underside defining an underside plane, the body further including a front surface having first and second partial boreholes;

a front plate mounted to the front surface of the body, the front plate including a first borehole and a second borehole, the first and second boreholes aligning with the first and second partial boreholes, respectively, and extending through the front plate at an angle ranging from about twenty degrees (20°) to about sixty degrees (60°) relative to the horizontal middle plane;

a first fixation element having a first head portion and a first shaft portion, the first head portion positioned in the first borehole and the first partial borehole and positioned between the upper and underside planes in an assembled configuration, the first shaft portion sized and configured to engage the first vertebral body;

a second fixation element having a second head portion and a second shaft portion, the second head portion positioned in the second borehole and the second partial borehole and positioned between the upper and underside planes in the assembled configuration, the second shaft portion sized and configured to engage the second vertebral body; and a securing plate fastened to the front plate to at least partly cover the first and second head portions and prevent the first and second fixation elements from moving out of the first and second boreholes, respectively.

41. The intervertebral implant according to claim 40, wherein the front surface of the body includes a recess for receiving the front plate.

42. An intervertebral implant for insertion into an intervertebral disc space between endplates of first and second vertebral bodies, the implant comprising:

a body portion including a left side surface, a right side surface, a front surface having first and second partial boreholes, a rear surface, an upper side having teeth suitable for abutting the end plate of the first vertebral body, the upper side defining an upper plane, an underside having teeth suitable for abutting the end plate of the second adjacent vertebral body, the underside defining an underside plane;

a front plate operatively coupled to the front surface of the body, the front plate including a first borehole and a second borehole having respective openings, the first and second boreholes being aligned with the first and second partial boreholes, respectively;

first and second fixation elements being anchorable within the first and second boreholes and partial boreholes, respectively, the first and second fixation elements having first and second heads and first and second shafts, respectively, the first and second heads and the first and second boreholes and partial boreholes positioned substantially between the upper and underside planes in an assembled configuration, the first and second shafts being positioned substantially on an opposite side of the upper and underside planes, respectively, in the assembled configuration; the implant further comprising a securing plate operatively connectable to the front plate in such a manner that the first and second boreholes of the front plate and the first and second heads are covered at least partly by the securing plate.

43. The intervertebral implant according to claim 42, wherein the front plate is received within a recess formed in the body portion.

\* \* \* \* \*